(12) United States Patent  (10) Patent No.: US 8,768,024 B1
Zingman et al.  (45) Date of Patent: Jul. 1, 2014

(54) SYSTEM AND METHOD FOR REAL TIME DETECTION OF VILLI TEXTURE IN AN IMAGE STREAM OF THE GASTROINTESTINAL TRACT

(71) Applicant: Given Imaging Ltd., Yoqneam (IL)

(72) Inventors: Igor Zingman, Constance (DE); Ofra Zinaty, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 0 days.

(21) Appl. No.: 13/907,076

(22) Filed: May 31, 2013

Related U.S. Application Data (63) Continuation of application No. 13/116,447, filed on May 26, 2011, now abandoned.

(60) Provisional application No. 61/350,076, filed on Jun. 1, 2010.

(51) Int. Cl.
*G06K 9/00* (2006.01)

(52) U.S. Cl.
USPC ............................. 382/128; 348/45; 600/101

(58) Field of Classification Search
USPC ................. 382/100, 128, 129, 130, 131, 132, 382/168–172, 181, 190, 195; 128/922; 378/4–27; 600/101, 112; 33/544; 348/45, 68
See application file for complete search history.

(56) References Cited

U.S. PATENT DOCUMENTS

| | | | |
|---|---|---|---|
| 4,278,077 A | 7/1981 | Mizumoto | |
| 4,936,823 A | 6/1990 | Colvin et al. | |
| 5,604,531 A | 2/1997 | Iddan et al. | |
| 5,697,384 A | 12/1997 | Miyawaki et al. | |
| 5,993,378 A | 11/1999 | Lemelson | |
| 6,240,312 B1 | 5/2001 | Alfano et al. | |
| 7,009,634 B2 | 3/2006 | Iddan et al. | |
| 7,236,623 B2 * | 6/2007 | Chapoulaud et al. | 382/133 |
| 7,684,599 B2 * | 3/2010 | Horn et al. | 382/128 |
| 7,953,261 B2 * | 5/2011 | Nishimura et al. | 382/128 |
| 2001/0051766 A1 * | 12/2001 | Gazdzinski | 600/309 |
| 2002/0103417 A1 | 8/2002 | Gazdzinski | |
| 2003/0167000 A1 | 9/2003 | Mullick et al. | |
| 2003/0208107 A1 | 11/2003 | Refael | |
| 2004/0249291 A1 * | 12/2004 | Honda et al. | 600/476 |
| 2006/0074275 A1 | 4/2006 | Davidson et al. | |
| 2007/0053557 A1 * | 3/2007 | Cahill et al. | 382/128 |
| 2007/0135715 A1 * | 6/2007 | Inoue et al. | 600/477 |
| 2007/0165932 A1 * | 7/2007 | Nishimura et al. | 382/128 |
| 2007/0255095 A1 * | 11/2007 | Gilreath et al. | 600/102 |
| 2007/0292011 A1 * | 12/2007 | Nishimura et al. | 382/128 |
| 2010/0046816 A1 * | 2/2010 | Igual-Munoz et al. | 382/128 |

* cited by examiner

*Primary Examiner* — Anand Bhatnagar
(74) *Attorney, Agent, or Firm* — Pearl Cohen Zedek Latzer Baratz LLP (57) ABSTRACT

A method and system for automatically detecting villi texture in in-vivo images. In-vivo images may be received from an in vivo imaging capsule, and at least one image may be selected for analysis. Textural details may be extracted, for example using morphological top hat transforms. The image may be divided into segments or patches. The patches may be pruned using a set of threshold conditions, which are calculated based on grayscale or color statistics of the patches. The patches may be classified as containing villi texture or not based for example on rotation-invariant textural features computed in the Fourier domain. A sum, score or rating for the image may be calculated based on the classification of each patch. The final score of the image may be averaged over a number of, for example, consecutive images, and the score may be used for detecting entry into the small bowel and segmenting the image stream to anatomical regions.

14 Claims, 5 Drawing Sheets

SYSTEM AND METHOD FOR REAL TIME DETECTION OF VILLI TEXTURE IN AN IMAGE STREAM OF THE GASTROINTESTINAL TRACT

CROSS-REFERENCE TO RELATED APPLICATIONS

This application is a continuation of U.S. patent application Ser. No. 13/116,447, filed May 26, 2011, which claims benefit of U.S. Provisional Patent Application No. 61/350,076, filed Jun. 1, 2010, all of which are incorporated herein by reference in their entirety.

FIELD OF THE INVENTION

The present invention relates to a method and system for real-time image processing of an image stream captured in-vivo. More specifically, the present invention relates to systems and methods for detecting villi structures in an image stream of the gastrointestinal (GI) tract.

BACKGROUND OF THE INVENTION

In-vivo imaging methods, such as performed by an in-vivo imaging system including an ingestible capsule, may be used to image body lumens within a patient. The imaging system may capture and transmit, for example, images of the gastrointestinal (GI) tract to an external recording device, while the capsule passes through the GI lumen. The capsule may capture images in variable frame rates of, for example, 4-40 frames per second. Large numbers of images, for example 100,000 to 300,000 images, may be collected for viewing during the imaging procedure, and may also be viewed and/or processed in real time. The images may be combined in sequence, and an image stream or movie of, for example, 30-120 minutes in length, may be presented to a user.

It would be desirable to provide a user, for example a physician, an indication of the capsule's current position in the body lumen. For example, it may be useful to indicate whether an ingestible capsule is in the stomach or has passed to the small bowel, or whether the capsule entered the colon.

SUMMARY OF THE INVENTION

Embodiments of the present invention include a system and computer-implemented method for detecting villi texture in in-vivo images. A stream of in-vivo images may be received from an in vivo imaging capsule, and at least one image from the stream may be selected for villi texture analysis. Textural details in the selected image may be extracted, and/or background may be removed, for example using morphological Top-Hat Transforms. In some embodiments, the image may be divided into patches for further processing.

The patches may be filtered out or pruned according to a set of predetermined threshold conditions, which may be calculated based on grayscale or color statistics of the image. In some embodiments, the filtered patches (the patches which were not pruned) may be further classified as containing villi texture or not (or a sufficient amount of villi structures). A Sum score may be calculated for the image, for example by counting the amount of patches in the image that received a positive villi classification. In one embodiment, a processor may determine if the image includes villi texture, for example by determining whether the image contains a sufficient amount of villi patches (e.g., above a predetermined threshold number). In some embodiments, if the image includes villi texture, an indication may be displayed to a user.

In some embodiments, the method may be used to segment an image stream, and/or indicate in which anatomical organ the image was captured. For example, upon detection of villi texture in at least one image, an indication to a user may be provided, that the image was captured in the small bowel or that the entrance to the small bowel has been detected. Additional regions or anatomical segments may be used, for example images may be assigned to a gastric region, a small bowel region, a colon region, and other regions.

In some embodiments, the method may include calculating an averaged final score for an image, based on the sum scores of a number of images, for example a number of consecutive images which may be before or after the current image in the original image stream or in the subset of images selected for analysis. The averaged final score may be calculated based on a predetermined number of consecutive images, or for selected images captured during a predetermined period of time.

According to some embodiments, rotation-invariant ring features may be extracted in a Fourier domain from each patch, and used for classifying the filtered patches as containing villi structures (e.g., a sufficient amount of villi structures) or not.

The detection operation may continue throughout the medical imaging procedure, however, some embodiments may allow stopping the detection operation upon villi texture detection.

In some embodiments, transitions between anatomical regions in the gastrointestinal tract may be detected based on the villi structure detection, for example a transition from the gastric region to the small bowel region may be detected based on villi texture detection, and a transition from the small bowel to the colon region may be detected upon detecting a sequence of images with no villi texture, after villi texture has been detected earlier in the image stream.

BRIEF DESCRIPTION OF THE DRAWINGS

The principles and operation of the system and method according to the present invention may be better understood with reference to the drawings, and the following description, it being understood that these drawings are given for illustrative purposes only and are not meant to be limiting, wherein.

It will be appreciated that for simplicity and clarity of illustration, elements shown in the figures have not necessarily been drawn to scale. For example, the dimensions and/or aspect ratio of some of the elements may be exaggerated relative to other elements for clarity. Further, where consid-

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Some embodiments of the present invention are directed to a swallowable in-vivo device, such as an autonomous swallowable capsule. Other embodiments need not be swallowable or autonomous, and may have other shapes or configurations. Devices according to embodiments of the present invention, including imaging, receiving, processing, storage and/or display units suitable for use with embodiments of the present invention, may be similar to embodiments described in US Patent Application Publication Number 2006/0074275, entitled "SYSTEM AND METHOD FOR EDITING AN IMAGE STREAM CAPTURED IN-VIVO", U.S. Pat. No. 5,604,531 to Iddan et al., entitled "In-vivo Video Camera System", and/or in U.S. Pat. No. 7,009,634 to Iddan et al., entitled "Device for In-Vivo Imaging", each assigned to the common assignee of the present application. Of course, devices and systems as described herein may have other configurations and other sets of components. Devices, systems and methods according to some embodiments of the present invention may be similar to the commercial PillCam® SB2 or PillCam® Colon capsules and the associated data recorders and RAPID® workstation provided by Given Imaging, Ltd.

Figure 1:
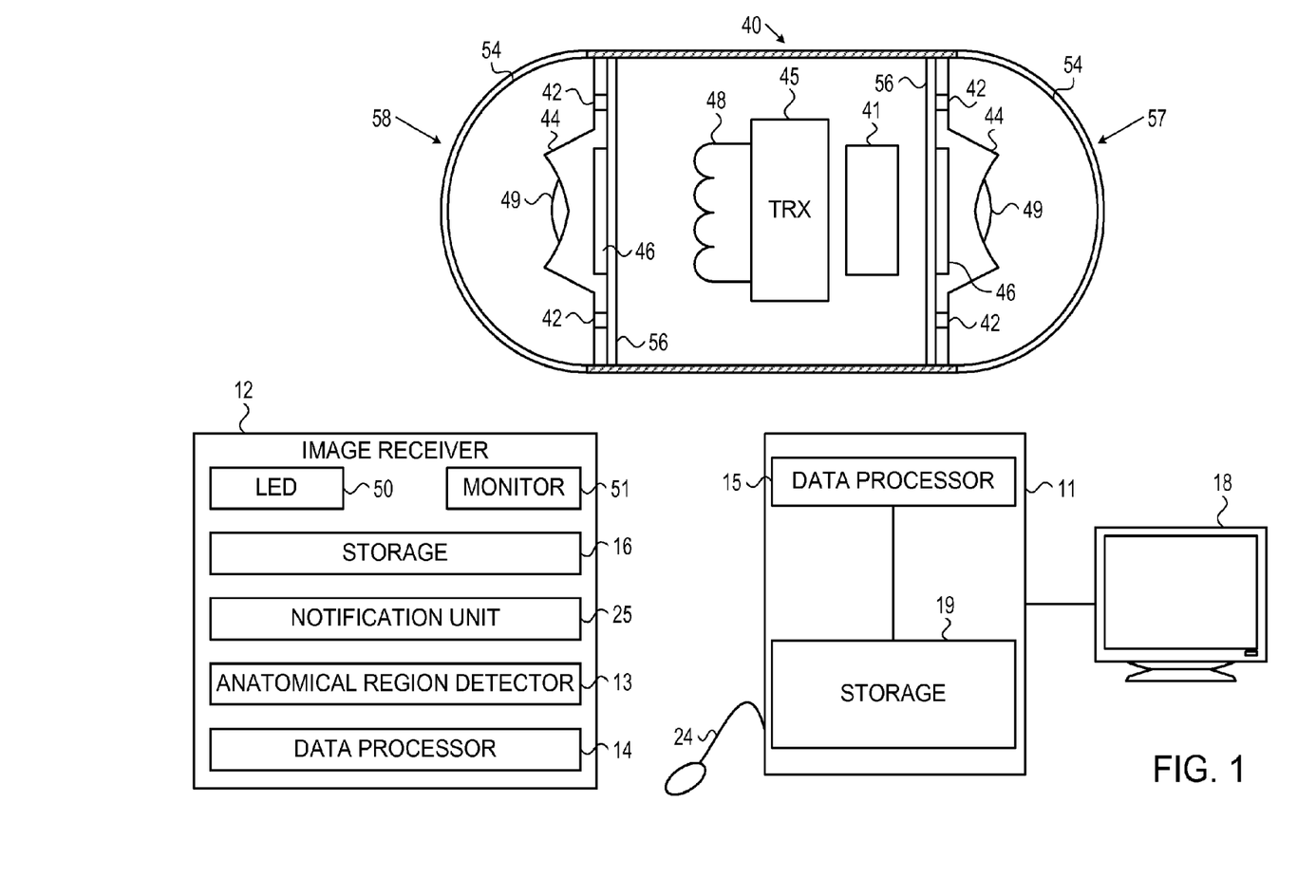
FIG. 1 shows a schematic diagram of an in-vivo imaging system according to an embodiment of the present invention.

Reference is made to FIG. 1, which schematically illustrates an in-vivo imaging system according to an embodiment of the invention. According to some embodiments, the system may include a device, for example, a capsule 40. Capsule 40 may be a swallowable in-vivo capsule, but other sorts of devices or suitable implementations may be used. According to one embodiment, capsule 40 may communicate with an external receiving and display system to provide display of data, control, or other functions. For example, power may be provided by an internal battery 41 or a wireless receiving system. Other embodiments may have other configurations and capabilities.

Capsule 40 may include one or more imagers 46 for capturing images, one or more illumination sources 42 for illuminating the body lumen, and a transmitter 45 for transmitting image data and possibly other information to a receiving device such as receiver 12. Transmitter 45 may include receiver capability, for example, to receive control information. In some embodiments, the receiver capability may be included in a separate component. An optical system, including, for example, lenses 49, lensholders 44 or mirrors, may aid in focusing reflected light onto the imagers 46. The lenholders 44, illumination units 42, and imagers 46 may be mounted on a substrate 56. An imaging head 57 and/or 58 may include the optical system, optical dome 54, imager 46, illumination units 42, and substrate 56.

Preferably, located outside the patient's body in one or more locations, are an image receiver 12, preferably including an antenna or antenna array, an image receiver storage unit 16, one or more data processors 14, 15, a data processor storage unit 19, and an image monitor 18, for displaying, for example, the images recorded by the capsule 40. Preferably, the image receiver 12, data processor 14 and image receiver storage unit 16 are small and portable, and are worn on the patient's body during recording of the images. The data processor 15, data processor storage unit 19, and image monitor 18 may be included in a computer or workstation 11, or may be included in the image receiver.

According to embodiments of the present invention, data processor 14 may receive images and telemetry data received by image receiver 12, for example in real time, or with a minimal delay. According to an embodiment of the invention, the data processor 14 may include an anatomical region detector 13 for determining an anatomical region in which an image was captured. Anatomical region detector 13 may be an anatomical region processor and may be implemented by data processor 14. While the anatomical region detector is shown in FIG. 1 as being separate from and connected to processor 14, in some embodiments anatomical region detector may be implemented as a set of code or instructions executed by, for example, processor 14 (or another processor such as processor 15). Anatomical region detector may be or may include one or more dedicated processors. The anatomical region detector 13 may evaluate the degree or occurrence in each frame of qualities based on each of a plurality of pre-defined criteria defined for example in the anatomical region detector 13 or in a separate storage unit. For example, the anatomical region detector 13 may process the images and/or the telemetry data, and determine, for example in real time, whether images or portions thereof are captured in the gastric region, in the small bowel region of the gastrointestinal tract, or in a different region (e.g. the colon). In some embodiments, a series of steps and pre-defined criteria and rules may be used to determine the anatomical region in which the image was captured. For example, anatomical region detector 13 may determine whether an image includes villi structures, which are typically found in the small bowel. If villi structures are detected in one or more images from an image stream, the anatomical region detector 13 may determine that the capsule has transited to the small bowel. If no villi structures are detected, or if a small amount of villi structures are detected in an image stream or a portion thereof (e.g., compared to a threshold amount), for example over a predetermined period of time of image capturing, or over a predetermined number of consecutive images, anatomical region detector 13 may determine that the capsule is capturing images in the stomach, or that the capsule has passed on to the colon. A threshold for determining whether a sufficient amount of villi structures is present in an image stream or a portion thereof may be determined, for example empirically. For example, a threshold condition for deciding that no villi were detected (or an insufficient amount of villi structures were detected), may be that the sequence of images in which no villi were detected is sufficiently long, e.g. a sequence of over one or two hours of captured images, or a sequence of over 50,000 images.

A score, rating, or measure may be calculated by anatomical region detector 13 for example for each image received by image receiver 12, or for selected images. For example, in some embodiments, images for processing by anatomical region detector 13 may be selected from a number of consecutive images (e.g., only one of every 5 images may be processed) or from a set of images received within a predetermined time period (e.g. 1 minute). In some embodiments, the anatomical region detector 13 may generate a simplified representation (e.g., a derived value or rating, such as an integer 0-100) of more complex characteristics of an image or a portion of an image (e.g., criteria, such as, color variation, appearance of certain textural or structural patterns, light intensity of the image or portions thereof, etc.). A score may include any rating, rank, hierarchy, scale or relative values of features or criteria. Typically a score is a numerical value, for example, a number from 1 to 10, but need not be limited as such. For example, scores may include, for example, letter (A, B, C, . . . ), signs or symbols (+, −), computer bit values (0, 1), the results of one or more decisions or conditions (yes no), for example, indicated by the status of one or more computing flags. Scores may be discrete (non-continuous) values, for example, integers, a, b, c, etc., or may be continuous, for example, having any real value between 0 and 1 (subject to the precision of computer representation of numbers). Any interval between consecutive scores may be set (e.g., 0.1, 0.2, . . . , or 1, 2, . . . , etc.) and scores may or may not be normalized.

Scores for each frame or one or more portions thereof may be stored with the frames in the same database (e.g., image receiver storage unit 16). The scores may be defined, e.g., in a header or summary frame information package, for example with the data in an initial image stream. Alternatively or additionally, the scores may be stored in a database separate from the images with pointers pointing to the images.

Figure 5:
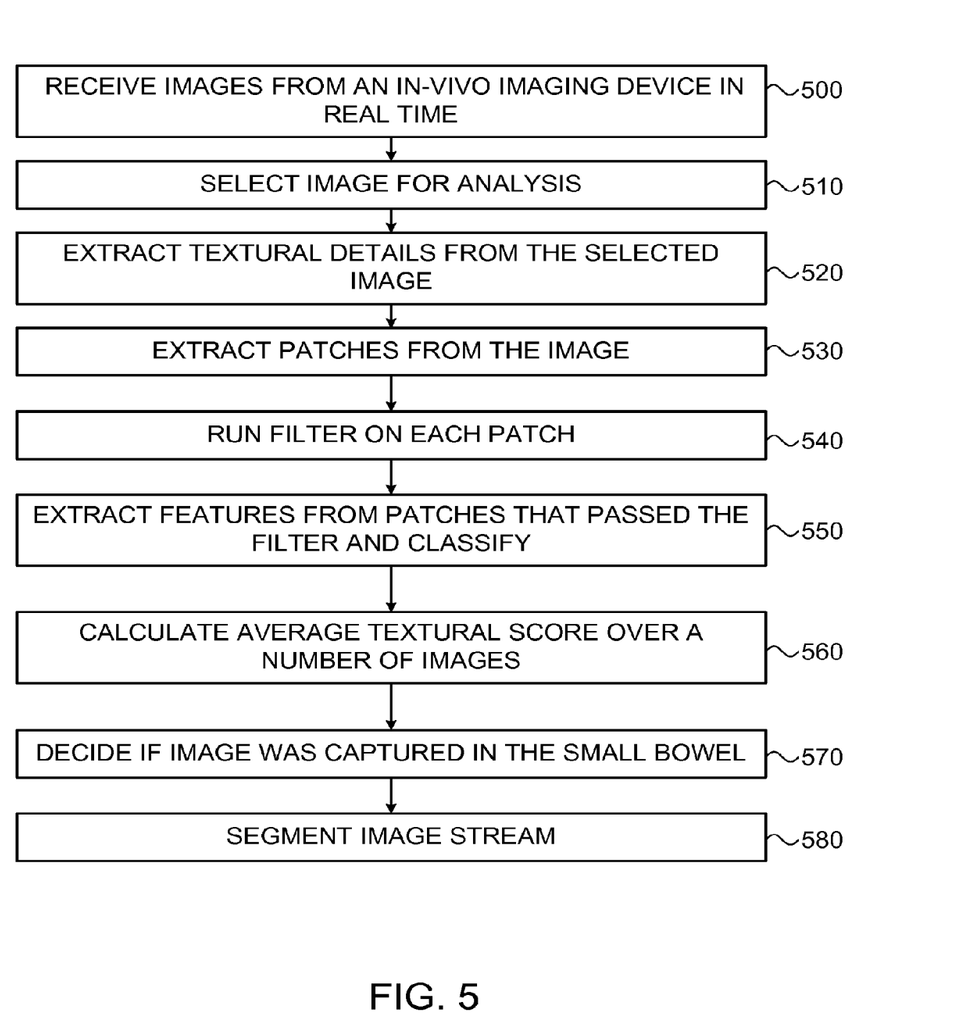
FIG. 5 is a flowchart of a method for segmenting an image stream according to an embodiment of the present invention.

In one embodiment, anatomical region detector 13 may assign a single combined score, e.g., a scalar value, rating each frame or group of frames based on predetermined criteria or steps, for example as described in FIG. 5. The score may indicate whether the image is a small bowel image or a stomach (gastric) image. For example, a value of '0' (zero) may be assigned to images which are suspected to be stomach images, while a value of '1' (one) may be assigned to images which are suspected to be small bowel images. In another embodiment, anatomical region detector 13 may assign a probability value to the image, for example a value of '53' may indicate that the detector calculated 53% probability of the image to be a small bowel image. Other values may be assigned, and other regions may be determined by anatomical region detector 13.

The scores or measures may be absolute or relative to each other, and may be calculated based on a sequence of frames or on a single frame. The absolute score(s) for each frame or portion of frame may be a value associated with the criteria for the single frame. The relative score(s) for each frame or for a portion of frame may be a change in the value associated with the criteria relative to the value associated with the criteria for a previous or adjacent frame. Both absolute and relative scores may or may not be scaled (normalized). Scores may be scaled with a different scaling factor, for example, for images captured in different frame capture rates.

The original image stream may be divided into patches, portions or segments. A patch, portion or segment may be defined based on, for example, determination of a small bowel image or a gastric image by anatomical region detector 13.

According to one embodiment, anatomical region detector 13 may process images or portions of images from one or more image streams captured by one or more imagers 46. For example, a double-headed capsule 40 may capture two image streams using two separate optical systems. The received image streams may be processed separately. For example, each stream may be processed as a separate stream, and for each image anatomical region detector 13 may determine independently in which anatomical region the image was captured. In other embodiments, streams may be merged, for example images from two or more streams may be sorted chronologically according to the capture time of the images and merged into a single stream, then processed as a single image stream. Other sorting methods are possible, for example based on different image parameters such as similarity between images, or based other scores assigned to the images by different filters, or detectors (e.g. pathology or abnormality detectors). The merged stream may be processed as one stream (e.g., anatomical region detector 13 may sequentially process images from the merged stream instead of separately from each stream). In some embodiments, images may be processed simultaneously, for example using more than one processor in parallel processing.

According to one embodiment of the invention, data processor 15, data processor storage unit 19 and monitor 18 may be part of a personal computer or workstation 11 which includes standard components such as a processor, a memory, a disk drive, and input-output devices, although alternate configurations are possible, and embodiments of the system and method of the present invention may be implemented on various suitable computing systems. An input device 24 may receive input from a user (e.g., via a pointing device, click-wheel or mouse, keys, touch screen, recorder/microphone, other input components) and send corresponding commands to trigger control of the computer components, e.g., data processor 15.

Data processors 14 and 15 may include one or more standard data processors, such as a microprocessor, multi-processor, accelerator board, or any other serial or parallel high performance data processor. Image monitor 18 may be a computer screen, a conventional video display, or any other device capable of providing image or other data. In some embodiments, an image and/or text display 51 may be provided in image receiver 12, in addition to or instead of image monitor 18.

Preferably, the imager 46 is a suitable ccomplementary metal-oxide-semiconductor (CMOS) camera, such as a "camera on a chip" type CMOS imager specified by Given Imaging Ltd. of Israel and designed by Photobit Corporation of California, USA. In alternate embodiments, the imager 46 may be another device, for example, a charge-coupled device (CCD). The illumination source 42 may be, for example, one or more light emitting diodes, or another suitable light source.

During an in vivo imaging procedure, imager 46 may capture images and send data representing the images to transmitter 45, which transmits images to image receiver 12 using, for example, electromagnetic radio waves. Image receiver 12 may transfer the image data to image receiver storage unit 16. In some embodiments, image data stored in storage unit 16 may be sent and processed immediately, e.g. in real time or substantially in real time, in the data processor 14. In other embodiments, after a certain period of time of data collection, the image data stored in storage unit 16 may be sent to the data processor 15 or the data processor storage unit 19. For example, the image receiver storage unit 16 may be taken off the patient's body and connected to the personal computer or workstation which includes the data processor 15 and data processor storage unit 19 via a standard data link, e.g., a serial or parallel interface of known construction.

Data processor 14 may analyze the data, for example, by activating anatomical region detector 13, and may store the result, for example per image. In some embodiments, the result may be provided to a user in real time, for example an indication or notification that the capsule 40 has passed from the stomach to the small bowel may be provided to the user. In one embodiment, a notification unit 25 may activate a sound alert, illuminate an LED 50, and/or display a message on an image monitor/screen 51 which may be operationally connected to data processor 14 or to image receiver 12. Such indication may be useful for a patient during an imaging procedure, for example an indication of the capsule's transit into the small bowel may induce the patient to take a certain medication or perform another step related to the medical procedure. The notification may indicate, for example, that the imaging device has entered a specific organ or transited into a specific region of the gastrointestinal tract (e.g., the small bowel), or that the imaging device entered the organ at or near the time the relevant image was captured. In some embodiments, the notification may be made in real time to a user, while other embodiments allow indication at a later time, for example an indication may be provided to a user reviewing the image stream after the procedure has been completed that the capsule transited into a certain region or organ.

Data processor 14 may execute or operate software or code (e.g., stored in storage 16) which, in conjunction with basic operating software such as an operating system and device drivers, controls the operation of data processor 14. According to one embodiment, the software controlling data processor 14 may include code written, for example, in the C++ language and possibly alternative or additional languages, and may be implemented in a variety of known methods.

The image data collected and stored may be stored indefinitely, transferred to other locations, manipulated or analyzed. A health professional may use the images to diagnose pathological conditions of, for example, the GI tract, and in addition, the system may provide information about the location of these pathologies. While using a system where the data processor storage unit 19 first collects data and then transfers data to the data processor 15, the image data is not viewed in real time. When using a system in which data processor 14 receives the data by data receiver 12 and processes or partially processes immediately (e.g., substantially upon image receipt, the image may be processed), real time or quasi-real time viewing is possible.

According to one embodiment, the capsule 40 may collect a series of still images as it traverses the GI tract. The images may be later presented as, for example, a stream of images or a moving image of the traverse of the GI tract. One or more in-vivo imager systems may collect a large volume of data, as the capsule 40 may take several hours to traverse the GI tract. The imager(s) 46 may record images at a rate of, for example, two to forty images per second each (other rates, such as four frames per minute, may be used). The imager(s) 46 may have a fixed or variable frame capture and/or transmission rate. When the imager(s) 46 have a variable or adaptive frame rate (AFR), the imager(s) 46 may switch back and forth between frame rates, for example, based on parameters, such as the capsule 40 speed, its estimated location, similarity between consecutive images, or other criteria. Thousands of images, for example, over 300,000 images, may be recorded. The image recordation rate, the frame capture rate, the total number of images captured, the total number of images selected for the edited moving image, and the view time of the edited moving image, may each be fixed or varied.

Preferably, the image data recorded and transmitted by the capsule 40 is digital color image data, although in alternate embodiments other image formats may be used. In an exemplary embodiment, each frame of image data includes 256 rows of 256 pixels each, each pixel including bytes for color and brightness, according to known methods. For example, in each pixel, color may be represented by a mosaic of four sub-pixels, each sub-pixel corresponding to primaries such as red, green, or blue (where one primary is represented twice). The brightness of the overall pixel may be recorded by a one byte (i.e., 0-255) brightness value. According to one embodiment, images may be stored sequentially in data processor storage unit 19 and/or in image receiver storage unit 16. The stored data may include one or more pixel properties, including color and brightness.

While, preferably, information gathering, storage and processing are performed by certain units, the system and method of the present invention may be practiced with alternate configurations. For example, the components gathering image information need not be contained in a capsule, but may be contained in any other vehicle suitable for traversing a lumen in a human body, such as an endoscope, stent, catheter, needle, etc.

Data processor storage unit 19 may store a series of images recorded by a capsule 40. The images the capsule 40 records as it moves through a patient's GI tract may be combined consecutively to form a moving image stream or movie.

Figure 2A:
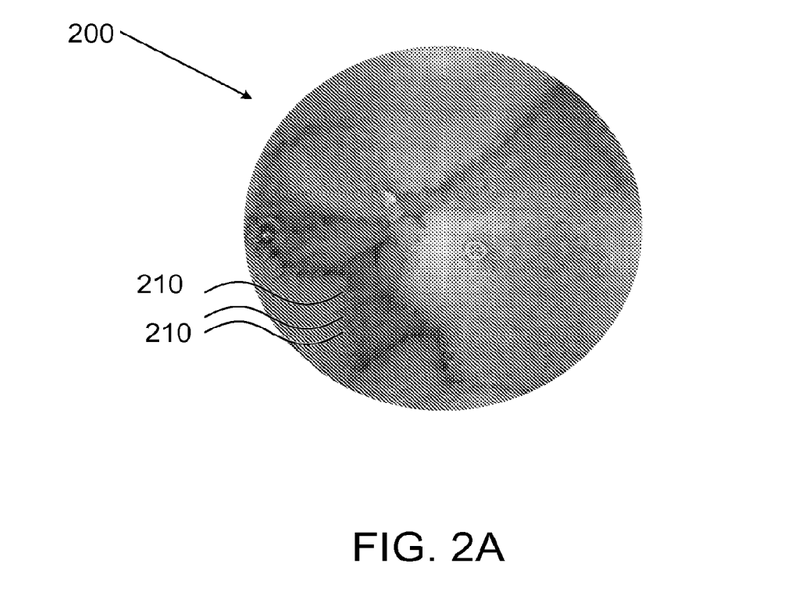
FIG. 2A is an exemplary small bowel image depicting villi structures according to an embodiment of the present invention.
Figure 2B:
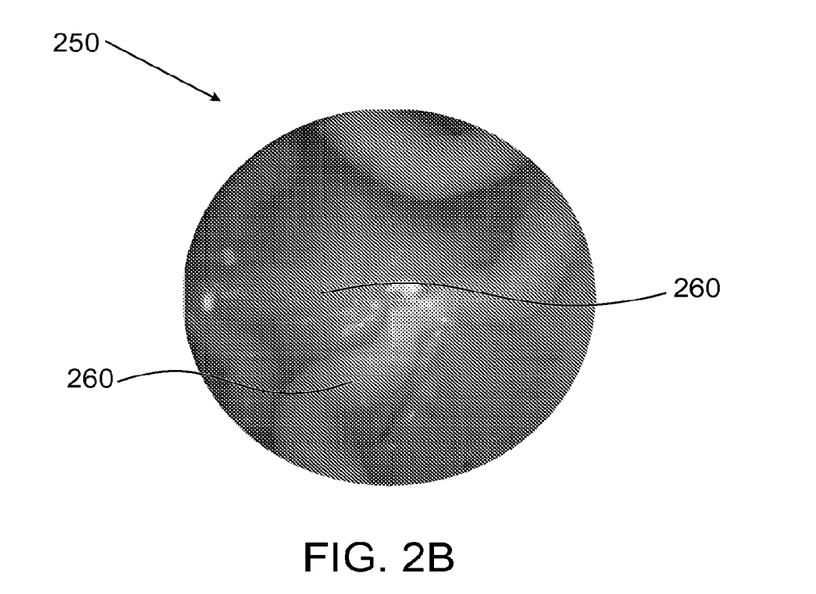
FIG. 2B is an exemplary gastric region image according to an embodiment of the present invention.

Reference is now made to FIGS. 2A and 2B, which depict an exemplary in vivo image of the small bowel (2A) and an exemplary in vivo image of the gastric region (2B). Image 200 includes numerous villi patterns 210, which are repeated hair-like structures, typically protruding from the mucosa of the small bowel. Detecting villi structures may indicate that images captured by the imaging device were captured in the small bowel. If no villi structures are detected in a series of consecutive images, or if a small amount of villi structures is detected (e.g., smaller than a predetermined threshold amount), several different scenarios are possible. For example, the imaging device may have captured these images in a different organ or segment of the body lumen (e.g. not in the small bowel), for example in the stomach or the colon, where no villi are typically found. In another example, the images may have been captured in the small bowel, but due to blurring, turbid media and/or content which may be present in the small bowel, the villi structures may be obscured or undetectable in the images. In yet another example, villi structures may not be present, even if the image was captured in the small bowel, for example if the patient has a certain medical condition such as Celiac or Crohn's disease. These diseases may damage the villi structures and cause them to disappear to some degree, e.g. partially, substantially or completely. In some embodiments, if no villi pattern is detected in any of the images captured during the whole imaging procedure, or if a small number of images containing villi pattern are detected throughout the imaging procedure or a portion thereof, an indication may be provided to the user advising an increased probability of these related medical conditions. In another example, the amount of patches indicated as containing villi in an image may be less than a predetermined threshold amount. In one embodiment, a text message may be displayed, for example on display 51, indicating that no villi pattern has been detected, or that an insufficient amount of villi patterns has been detected, or indicating that Celiac or Crohn's disease is suspected and should be further investigated. In some embodiments, the amount of villi patterns detected may be presented to a user, for example displayed along a normal range or amount of villi patterns or patches including villi patterns in images which are expected to be found in the small bowel. Other alerts and display options are possible.

Image 250 shows an exemplary gastric image, which does not include villi structures. The tissue walls 260 are substantially smooth, with no visible villi structures.

In some embodiments, detecting the images which contain villi patterns may indicate that the imaging capsule has advanced from the stomach to the small bowel. Similarly, if no villi patterns are detected in images after villi patterns have already been detected over a sequence of images, it may be deduced that the capsule has exited the small bowel and continued to the colon. For example, a text message may be displayed on display 51, indicating that the capsule has exited the small bowel.

Figure 3:
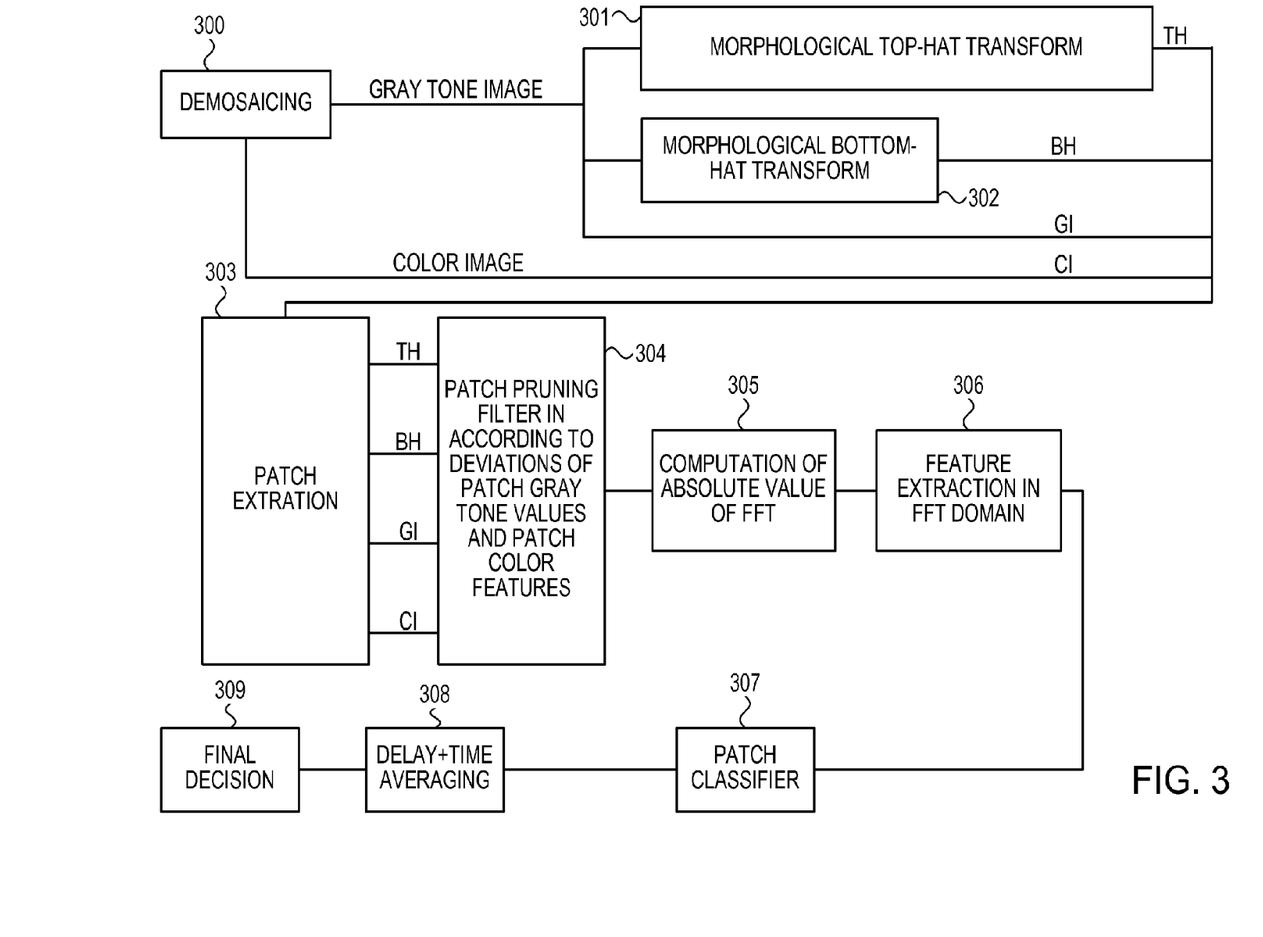
FIG. 3 is a block diagram of a method of detecting villi texture based on image processing in real time according to an embodiment of the present invention.

Reference is now made to FIG. 3, which depicts a flowchart of an algorithm for detecting a specific pattern in an image, e.g. a villi pattern. In step 300, an image is received from the in vivo device. The format may be, for example in raw Bayer mosaic data format. The image may be processed by performing de-mosaicing, and a color image may be generated, for example of 256×256 pixels. Other processing steps are possible, for example the image may be decompressed and/or descrambled before de-mosaicing. In addition, a gray tone image may be generated from the raw Bayer mosaic data. The image data may have other formats. The generated color images may have other sizes, for example 128×128 pixels, which may be generated, for example, by selecting one out of every 4 pixels. Generating a smaller-sized image may have an advantage of shorter processing time, in some embodiments without a substantial change to the sensitivity and specificity of the result.

Steps 301 and 302 include a pre-processing stage of the grayscale image. The pre-processing may include for example morphological white top-hat transforms 301 and/or black top-hat transforms 302 (also named "bottom hat" transforms). Other or no pre-processing may be used. The white top-hat and black top-hat transforms perform an operation that extracts small elements or details from the input images and emphasizes them, while the background and large elements are removed from the image. For example, f:E↦R is a grayscale image, mapping points from a Euclidean space or discrete grid E (such as R2 or Z2) into the Real numbers space. The white Top-hat transform of f is given by: $T(f) = f - f \circ b$, where $\circ$ denotes the opening transform. b(x) may be a grayscale or a flat structuring element. The details that may be extracted by the top-hat transforms can be controlled by the size of the structuring element b(x). Similarly, the black Top-hat transform (sometimes called a bottom-hat transform), is defined as the residual of a closing compared to the original signal $B(f) = f \bullet b - f$, where $\bullet$ denotes the closing operation. In some embodiments, only a white top-hat transform or only a black top-hat transform may be used in the preprocessing stage.

In one embodiment, a mask of 5×5 pixels may be used as a flat structuring element, which is typically processed faster than a grayscale structuring element. Different sizes of masks may be selected. However, the size of a typical feature in the pattern being sought may determine the minimal size of the mask. For example, a 5×5 pixel mask may be large enough to include a single villus structure, substantially without cropping it. Using this structuring element may allow the transform to keep details that are similarly sized in the image, while removing larger structures which may be irrelevant to the sought pattern. Other mask sizes may be selected, e.g. 7×7.

The output from the morphological preprocessing stage transforms provides the input for step 303, which includes dividing the image into a plurality of patches of size M×N pixels for further processing. The patches may be partially overlapping, which may cause longer processing time but may be more reliable than selecting non-overlapping patches. The typical size of the sought texture pattern in an image may determine the selected size of the patch. In one embodiment, patches of for example 32×32 or 64×64 pixels may be extracted from the image without overlapping between patches. The patches may be filtered out or pruned in step 304 according to selected characteristics or features of the patch grayscale and color values. In the pruning process, some of the patches may pass on to the next stage, while some may be filtered out. The set of filtered patches is typically a subset of the plurality of patches extracted for an image. For example, for each patch, one or more of the following parameters may be calculated: average R value of the patch (where R denotes the red pixels value of the RGB image), average G (green) value, average B (blue) value, average(G)/average(R), and average(B)/average(R). In another example, the pruning process may be based on logarithm of the color or the gray level images, to compensate for differences in lighting conditions. In addition, the deviation of the gray-scale values in the image may be calculated, for example by calculating the mean of the absolute change between each pixel's values to the average value of the patch. Each parameter may have a threshold condition which may be determined, for example, empirically based on a database of input image streams. Any learning algorithm may be used to determine the threshold conditions, for example a histogram of each parameter may be generated, and the range of values selected as the threshold condition may be determined by selecting a bottom value such that 99.5% of the values are above it, and a top value such that 99.5% of all values are below it. Based on the threshold of the parameters, it may be determined whether the patch is qualified to continue on to the next step or not. Each patch that did not pass the threshold conditions of step 304, may be assigned a value of 'zero' in step 304 (e.g., no villi texture was detected in this patch). Other values or scores may be assigned to indicate that the patch does not include detected villi structures.

Figure 4:
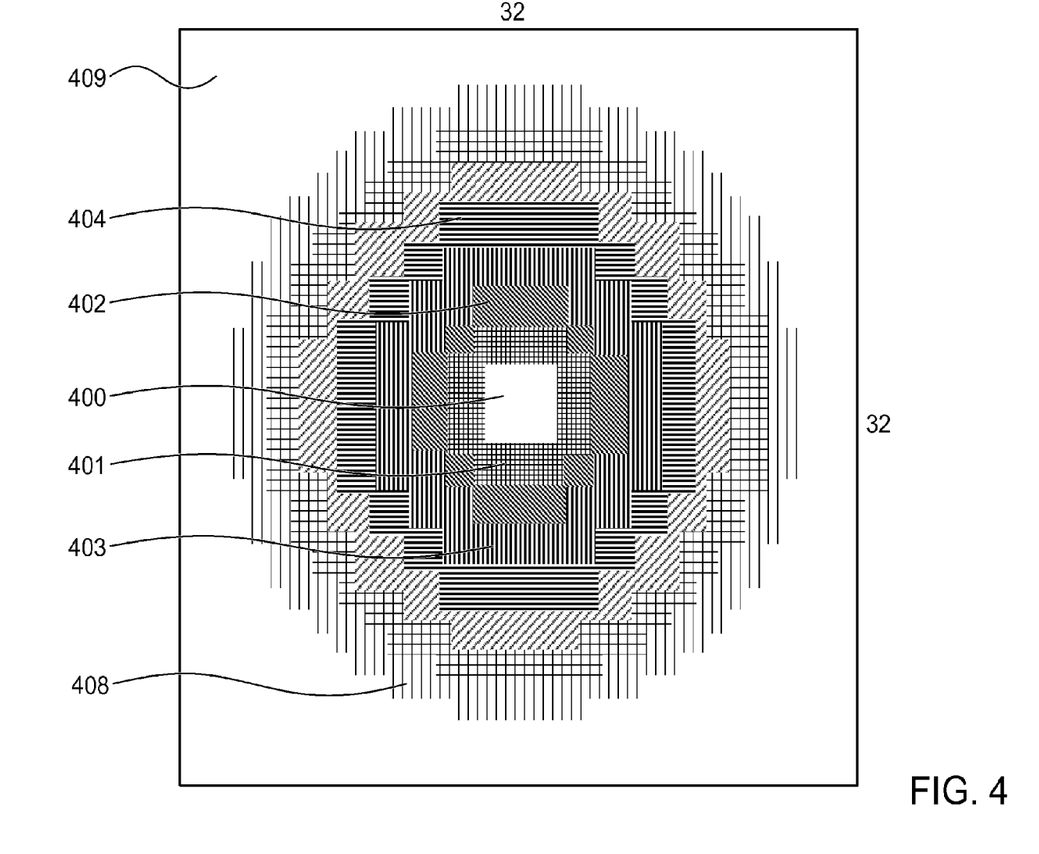
FIG. 4 is an exemplary ring filter according to an embodiment of the invention.

In step 305, Fast Fourier Transform (FFT) is performed on each patch that passed the threshold condition. The result may be used for extracting rotation-invariant textural features (step 306) by means of for example ring filters. For example, a maximum function may be applied to the FFT values along a number of rings or ring-like shapes, for example as shown in FIG. 4. The rings, e.g. rings 402, 403, 404 and 408, may be selected to cover substantially all pixels of the patch in the Fourier domain. In some cases, some ring features may be disregarded or ignored, due to their low discrimination ability. For example, excluding the highest frequency ring 409 and lowest frequency ring 401, along with the central DC point 400 in a patch of 32×32 pixels in the Fourier domain, may result in 13 rotation-invariant ring features. Other features may be selected and calculated, in addition to or instead of the ring features.

The features extracted from the FFT domain may provide the input to a classifier in step 307. The classifier may determine whether the patch includes the sought villi pattern or not. Some of the patches that passed the threshold condition will be assigned the value 'one' by the classifier in step 307, indicating that villi texture has been detected in these patches, and others may be assigned the value 'zero'. The values per patch may be stored, for example in a storage unit in image receiver 12 or in a different storage unit. In one embodiment, the number of patches from the whole image that are assigned the value 'one' may be counted (e.g., the number of patches in each image identified as including villi structure), and the total count may be stored per image, for example in image receiver storage unit 16.

In step 308 a delay and averaging operation may be performed. For each selected or analyzed image, a score may be calculated, by averaging over a sequence of images, the total count of number of patches that received a value 'one'. In some embodiments, the calculation may be performed for a predetermined number of sequential images before the current image (e.g. 10 or 25) and/or a predetermined number of images after it (e.g. 10 or 25). In this case, the calculation of the average score may be delayed until the images captured after the current image are received and processed, for example by anatomical region detector 13. In some embodiments, the calculation may be performed only on the predetermined number of previous images, e.g. 50, for example when using a single imaging system. When using, for example, a double-headed capsule (e.g. with two imaging systems) for an imaging procedure, 25 previous images captured by each head may be used. Other numbers of images may be used for the averaging operation, for example the number may depend on the frame capture rate of the capsule, and/or on the amount of time that passed since the start of the imaging procedure, or other considerations/parameters.

In step 309, based on the score calculated in step 308, a final decision may be determined based on one or more threshold conditions. If the average number of patches determined to include villi texture in a set of consecutive images (e.g., neighboring the current image) is high enough, for example above a predetermined threshold, the current image may be determined to be a small bowel image. Otherwise, the current image may be determined to be a stomach image. In some embodiments, a score combining a sequence of images need not be calculated, and the final decision may be determined based on whether the number of patches in a single image passed a threshold condition (for example, if villi pattern was detected in four or more patches of an image, the image may be determined to be a small bowel image). According to some embodiments, once a small bowel image has been detected, the algorithm may stop its operation (e.g., due to a physiological presumption that once the imaging capsule has advanced from the stomach to the small bowel, it will not go back again but rather continue to advance forward towards the colon). In other embodiments, the villi detection process may continue while the capsule is traversing the small bowel. In the colon there are typically no villi structures, therefore a transition from the small bowel to the colon may be determined based on detecting that no more villi structures are present in the images, for example in images captured after the small bowel has been detected.

Reference is now made to FIG. 5, which depicts a flowchart of a method according to an embodiment of the present invention. In step 500, images sent from an in vivo imaging device may be received, for example by an image receiver 12. The images may be received in real time (e.g., as soon as an image is captured, it is transmitted and received), substantially in real time, or with an introduced delay. The images may be captured and sent in different frame rates, for example the capsule may change its frame rate from time to time, and in some time periods two images per second may be received, while in other time periods 40 images per second may be received. In step 510, one or more images for analysis of villi structures may be selected from the received image stream. In some embodiments, each image received may be analyzed. Other embodiments may allow a subset of images to be analyzed, for example by selecting one image for analysis in every predetermined time period (e.g. one image every second), or one image in every predetermined number of images (e.g. one out of 10 received images). Image selection may also vary according to the frame capture rate of the capsule 40, or according to other parameters of the video stream. In some embodiments, images may be received from more than one imager simultaneously, e.g., in a double headed imaging capsule 40, images may be received from a first imaging system and a second imaging system. The selection of images in this case may be such that images are selected from both imaging systems, or from a single imaging system.

In step 520, a selected image may be processed to remove background and enhance certain textural details in the image. For example, a top-hat transform may be applied to the image, using a specific mask which will enhance small villi structures in the image, while substantially removing larger structures which may be present in the image. After the texture processing, segments or patches may be extracted from the result (step 530). The size of the segments or patches may be a predetermined constant, and may be dependent on the image resolution/size, and/or on the sought texture. The image may be divided into L patches of size M×N pixels for further processing. For example, the image may be divided into 64 patches of size 32×32 pixels each. In some embodiments, patches may be extracted such that each patch partially overlaps other patches to a certain degree, for example patches may have 30% or 50% overlap with neighboring patches.

In step 540, a filter or pruning process may be applied to each patch. The filter may include a set of threshold conditions which may be checked for each patch. In some embodiments, only patches that pass some or all of the threshold conditions may continue to a next stage of processing. Threshold conditions may be calculated, for example, based on the statistics of the grayscale or color features extracted from patches. Examples of threshold conditions include, but are not limited to, average R value of the patch (where R denotes the red pixels value of the RGB image), average G value, average B value, average(G)/average(R), and average (B)/average(R).

In step 550, features may be extracted from patches that passed the filter, for example ring features in the Fourier domain as described in step 306 of FIG. 3. A classifier may receive the extracted features, and determine for each patch whether villi structures are present in it. The result may be stored per patch, for example a simple score may be assigned by the classifier to each patch, e.g. a score of "zero" indicating no villi structures were identified, or a score of "one" indicating presence of villi structures in the patch. A total count of the number of patches per image that received a positive villi indication may be calculated and stored as a Sum score per image. Other methods of determining a summary score for an image based on patches to determine a final image score or rating may be used.

In step 560, the Sum score may be used to calculate an average score which will be used as a final score or rating of the image. In one embodiment, the score may be averaged based on Sum scores of the current image and its neighboring images. The final score may be, for example, an average of the Sum scores per image, averaged over a predetermined number of consecutive or adjacent images For example, the final score may be calculated by averaging the Sum scores of the current image and 49 previous images. Thus the final score for current image X may be an average of the Sum score of the current image X and the Sum scores of a predetermined number of previous and/or next images.

In some embodiments, the set of images averaged for the calculation of the averaged final score of a current image may include previous images and/or successive images. In this embodiment, the calculation of the averaged final score may be delayed until the Sum scores are calculated for the subsequent images.

In some embodiments, the images used for the calculation are only images which have been selected for analysis in step 510. Therefore, in embodiments in which not every image is analyzed, a set of "consecutive" images may include images which are not immediately sequential in the original image stream received from the capsule 40. The images may be consecutive or adjacent images, or neighboring images in the originally captured image stream, but in some cases there may be gaps between the images being averaged, for example if not all images from the original image stream are selected to be analyzed or processed for villi detection.

In step 570, it is determined whether an image includes the villi structure or not. This decision may be determined based on a threshold condition for the final score calculated in step 560. If the set of consecutive or sequential images include a sufficient average amount of patches with villi texture, then it may be determined that the image is a small bowel image. In some embodiments, if the final score passes a predetermined threshold, an indication of an anatomical transition of the imaging device may be provided, either in real time during the image capturing procedure, or at a later time for example when reviewing the image stream. The transition may include, for example, passage of the capsule 40 from the stomach region to the small bowel, or passage of the capsule 40 from the small bowel to the colon.

According to some embodiments, once a decision is taken that an image is a small bowel image, the analysis process may quit, since physiologically, it is unlikely that a capsule that passed into the small bowel will go back to the stomach or gastric region. In some embodiments, the analysis process may continue in the small bowel. For example, upon detecting that a predetermined number of consecutive images do not include the villi pattern, it may be determined that the capsule 40 has passed from the small bowel into the colon. The gastric, small bowel and colon regions may be segmented (step 580), e.g. a first image or sequence of images containing a sufficient amount of villi structures may indicate the entrance to the small bowel, and a first image or sequence of images indicating no villi structures (after the small bowel was detected) may indicate the entrance to the colon. Segmenting the image stream may include indicating landmark points or anatomical regions in the image stream, e.g. images corresponding to the stomach, images corresponding to the small bowel and images corresponding to the colon. The segmentation may include finer segments, for example images which were captured in the terminal ileum, images which were captured in the transverse colon, etc. In some embodiments, each image may be classified as belonging to a certain anatomical segment, e.g., the esophagus, the stomach, the small bowel, the ascending colon, the transverse colon, the descending colon or the rectum. Other anatomical segments may be indicated, and in some embodiments the user may select the anatomical segments he wishes to view or to segment the stream according to. Other segmentation methods of the gastrointestinal tract are possible.

The user may be notified or alerted, for example in real time using notification unit 25 which may be operationally connected to image receiver 12, that the capsule entered the small bowel, the colon, or other anatomical regions. In some embodiments the user need not be alerted in real time, for example the indication of villi detection may be used to segment the image stream to anatomical structures of the gastrointestinal tract at a later time, e.g., when a physician is reviewing the stream. In some embodiments, not all the above mentioned steps are essential and the method may be implemented using a subset of the steps.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

The invention claimed is:

1. A computer-implemented method for detecting an anatomical transition of an imaging device capturing in-vivo images, the method comprising:
   receiving a stream of in-vivo images from an in vivo imaging device;
   selecting an image from the images for analysis;
   extracting textural details from the selected image;
   dividing the image into patches;
   classifying at least a subset of the patches as containing villi texture or not;
   calculating a sum score of the image, based on the classification of each classified patch;
   calculating an averaged score of the image, by averaging the sum score of the image and sum scores of a set of adjacent images from the stream of in-vivo images; and
   based on the averaged score, detecting an anatomical transition of the imaging device.

2. The method according to claim 1 wherein extracting textural details from the selected image includes extracting textural details from at least a portion of the patches.

3. The method according to claim 1 comprising: detecting an anatomical transition based on the villi texture detection.

4. The method according to claim 1 comprising segmenting the image stream to at least a gastric region and a small bowel region.

5. The method according to claim 1 wherein the averaged score is calculated for a predetermined number of consecutive images.

6. The method according to claim 5 wherein the averaged score is calculated for selected images, said selected images captured by the imaging device during a predetermined period of time.

7. The method according to claim 1 further comprising if no villi texture is detected in a sequence of images or if the amount of detected villi texture is below a predetermined threshold, providing an indication to a user that the small bowel was not detected.

8. The method of claim 1, wherein the set of adjacent images includes previous images or successive images from the stream of images.

9. A system for automatically detecting villi texture in in-vivo images, the system comprising:

a receiver to receive a stream of in-vivo images from an in vivo imaging capsule;

a processor to:
- select an image from the stream for analysis;
- extract textural details in the selected image;
- dividing the image into patches;
- classifying at least a subset of the patches as containing villi texture or not;
- calculating a sum score of the image, based on the classification of each classified patch;
- calculating an averaged score of the image, by averaging the sum score of the image and sum scores of a set of adjacent images from the stream of in-vivo images; and
- based on the averaged score, detecting an anatomical transition of the imaging device.

10. The system of claim 9 comprising a notification unit to notify a user that entrance to the small bowel was detected.

11. The system of claim 9 wherein the processor is to segment the image stream based on the villi texture detection to at least a stomach region and a small bowel region.

12. The system of claim 9 wherein the processor is to prune the patches using a set of threshold conditions calculated based on grayscale or color image statistics to produce a set of filtered patches, the set of filtered patches being a subset of the plurality of patches.

13. A method for detecting an anatomical transition in an image stream, comprising:
- receiving a stream of in vivo images captured by an in vivo imaging device;
- selecting an image from the images for analysis;
- extracting textural details in the selected image;
- dividing the image into a plurality of patches;
- classifying at least a portion of the patches as containing villi texture or not;
- calculating a score for the image, based on the classification result of each classified patch;
- calculating an averaged score of the image, by averaging the sum score of the image and sum scores of a set of adjacent images from the stream of in-vivo images; and
- based on the averaged score, detecting an anatomical transition of the imaging device.

14. The method of claim 13 comprising detecting that the imaging device has entered the small bowel or colon based on the scores of a sequence of images.

* * * * *